United States Patent
Araki et al.

(10) Patent No.: US 6,824,358 B2
(45) Date of Patent: Nov. 30, 2004

(54) TURBO BLOOD PUMP

(75) Inventors: Kenji Araki, Miyazaki (JP); Hirofumi Anai, Oita (JP); Hiroyuki Maeda, Hiroshima (JP); Masafumi Sato, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 0 days.

(21) Appl. No.: 10/294,478

(22) Filed: Nov. 13, 2002

(65) Prior Publication Data

US 2004/0091354 A1 May 13, 2004

(51) Int. Cl.[7] .................................................. F01D 1/02
(52) U.S. Cl. ...................................... 415/206; 416/185
(58) Field of Search ............................... 415/206, 900; 416/185, 188, 223 R, 238, DIG. 2, 186 R, 223 B; 417/420

(56) References Cited

U.S. PATENT DOCUMENTS

| | | | | |
|---|---|---|---|---|
| 5,017,103 A | * | 5/1991 | Dahl | .......................... 417/420 |
| 5,863,179 A | * | 1/1999 | Westphal et al. | ........... 415/206 |
| 6,135,710 A | * | 10/2000 | Araki et al. | ................ 415/206 |
| 6,162,017 A | * | 12/2000 | Raible | ........................ 415/206 |
| 6,394,769 B1 | * | 5/2002 | Bearnson et al. | ........ 417/423.7 |

* cited by examiner

*Primary Examiner*—Edward K. Look
*Assistant Examiner*—James M. McAleenan
(74) *Attorney, Agent, or Firm*—Merchant & Gould P.C.

(57) ABSTRACT

A turbo blood pump having a small size, that is, a small amount of blood to be filled and capable of adjusting and maintaining the slight amount of flow, and a turbo blood pump in which hemolysis is not likely to occur even if it is used at a practically high rotational speed necessary to obtain a predetermined discharging ability. The turbo blood pump to be used includes a housing having an inlet port and an outlet port; and an impeller disposed rotatably in the housing; wherein the impeller includes at least a rotation shaft and an annular connection portion to which the plural vanes are attached. The vane is manufactured so that an inlet side part is in the skew position with respect to an outlet side part.

9 Claims, 4 Drawing Sheets

TURBO BLOOD PUMP

BACKGROUND OF THE INVENTION

1. Field of the Invention

The present invention relates to a liquid-transferring pump for medical use. More specifically, the present invention relates to a turbo blood pump for transferring blood by providing blood with thrust by the rotation of an impeller.

2. Description of the Related Art

Conventionally, in extracorporeal circulation in an operation using an artificial heart lung apparatus, etc., a roller blood pump has been used mostly. Recently, however, centrifugal blood pumps increasingly have been used. This is because, as compared with roller blood pumps, the centrifugal blood pumps (turbo blood pumps) have various advantages, for example, little damage to blood, etc. Furthermore, as compared with a driving portion of a conventional large size roller blood pump, the centrifugal blood pump may have a smaller driving portion. Therefore, the centrifugal blood can be disposed and carried easily.

However, when the centrifugal pumps are used in a clinical application, there have been the following problems to be solved. Firstly, the centrifugal blood pumps have a problem as to the amount of blood to be filled. In centrifugal blood pumps, in order to reduce hemolysis, driving at a low rotational speed is desired. However, if the rotational speed were reduced, it was necessary to increase the size of the pump in order to obtain the same discharging ability (liquid transferring amount). If the size of the blood pump were increased, the amount of blood to be filled was increased. As a result, the amount of blood for extracorporeal circulation is increased, thus burdening a patient more.

On the contrary, in order to obtain a sufficient amount of blood with a smaller-size pump, the impeller has to be rotated at high speed. In such a case, it is not possible to realize the reduction of hemolysis (damage to blood), etc.

Furthermore, if a centrifugal pump, in which the standard such as rotational speed, amount of liquid to be transferred, amount of liquid to be filled, etc. is set for an adult patient, is used for a child patient or a patient who cannot tolerate a large amount of blood circulation, the pump has to be used at the lower rotational speed, and it is difficult to adjust and maintain the amount of liquid to be transferred.

Furthermore, not a few of conventional centrifugal pumps have a structure in which blood tends to stagnate in the central portion of the lower surface of the impeller. When such a centrifugal pump is used, there arise some problems in that thrombus tends to be formed, and it is difficult to use such a pump for a long-time extracorporeal circulation, etc.

With the foregoing in mind, it is an object of the present invention to provide a blood pump avoiding the above-mentioned problems. That is, the first object of the present invention is to provide a turbo blood pump having a small size (blood to be filled is small) and capable of adjusting and maintaining a slight amount of flow. The second object of the present invention is to provide a turbo blood pump with little hemolysis even if it is used in a practically high rotational speed necessary to achieve a predetermined discharging ability.

SUMMARY OF THE INVENTION

In order to achieve the above-mentioned object, the turbo blood pump of the present invention includes a housing having an inlet port and an outlet port; and an impeller disposed rotatably in the housing. The impeller includes at least a rotation shaft, plural vanes and an annular connection portion. The plural vanes are connected to the annular connection portion in a part at the side of the outlet port, and some or all of the plural vanes are connected to the rotation shaft by a supporting member in a part at the side of the inlet port, and a vane inlet side line k of the plural vanes, which connects an inlet side upper end and an inlet side lower end of the plural vanes, is in the skew position with respect to the rotation shaft and a vane outlet side line l of the plural vanes, which connects an outlet side upper end and an outlet side lower end of the plural vanes.

Furthermore, it is preferable that the above-mentioned turbo blood pump of the present invention has the following embodiments. According to the first embodiment, the vane outlet side line l is in parallel with the rotation shaft. According to the second embodiment, an angle made by the vane inlet side line k and an axis intersecting the vane inlet side line k and parallel to the rotation shaft is set to be larger than an angle made by the vane outlet side line l and an axis intersecting the vane outlet side line l and parallel to the rotation shaft.

According to the third embodiment, an angle made by a vane upper surface line m that connects the inlet side upper end and the outlet side upper end, and an axis intersecting the vane upper surface line m and parallel to the rotation shaft is set to be smaller than an angle made by a vane lower surface line n that connects the inlet side lower end and the outlet side lower end, and an axis intersecting the vane lower surface line n and parallel to the rotation shaft.

According to the fourth embodiment, assuming a first circle passing the inlet side upper end, which is concentric with the outer periphery of the impeller, a tangent line p of the first circle, which passes an intersection point of the vane upper surface line m of one vane and the first circle, a second circle passing the outlet side lower end, which is concentric with the outer periphery of the impeller, and a tangent line q of the second circle, which passes an intersection point between the vane lower surface line n of the one vane and the second circle; an angle θ made by the tangent line p and the vane upper surface line m of the one vane is smaller than an angle ε made by the tangent line q and the vane lower surface line n of the one vane.

According to the fifth embodiment, the profile of the vane presents a shape of a curved surface that smoothly connects the vane inlet side line k and the vane outlet side line l, the shape of the curved surface is a shape obtained by shifting the vane inlet side line k that is in the skew position with respect to the rotation shaft along the radius direction toward the outer periphery of the impeller while allowing it to convolute until it becomes in parallel with the rotation shaft.

According to the sixth embodiment, the plural vanes are made of a first vane and a second vane, which have different areas. In this embodiment, the first vane and the second vane are disposed so that they are in a position of rotational symmetry with respect to the rotation shaft and the total number of the plural vanes is in the range from 4 to 8.

According to the seventh embodiment, a driving shaft having driving magnets at the side of the housing is provided outside the housing and the annular connection portion is housed in a pump chamber in the housing has driven magnets to be attracted by the driving magnets via the inner wall of the housing.

By using the turbo blood pump of the present invention, various problems mentioned above can be solved. Firstly, even in a liquid transferring pump with a small size (amount of blood to be filled is small), a large flow amount of liquid can be transferred. And by increasing the rotational speed, it is easy to adjust and maintain the amount of liquid to be transferred. Second, even if the liquid transferring pump operates at practically high rotational speed, the hemolysis degree is small, thus reducing the damage to the body. As a result, it is possible to be applied to a long time extracorporeal circulation.

DETAILED DESCRIPTION OF THE INVENTION

Figure 1:
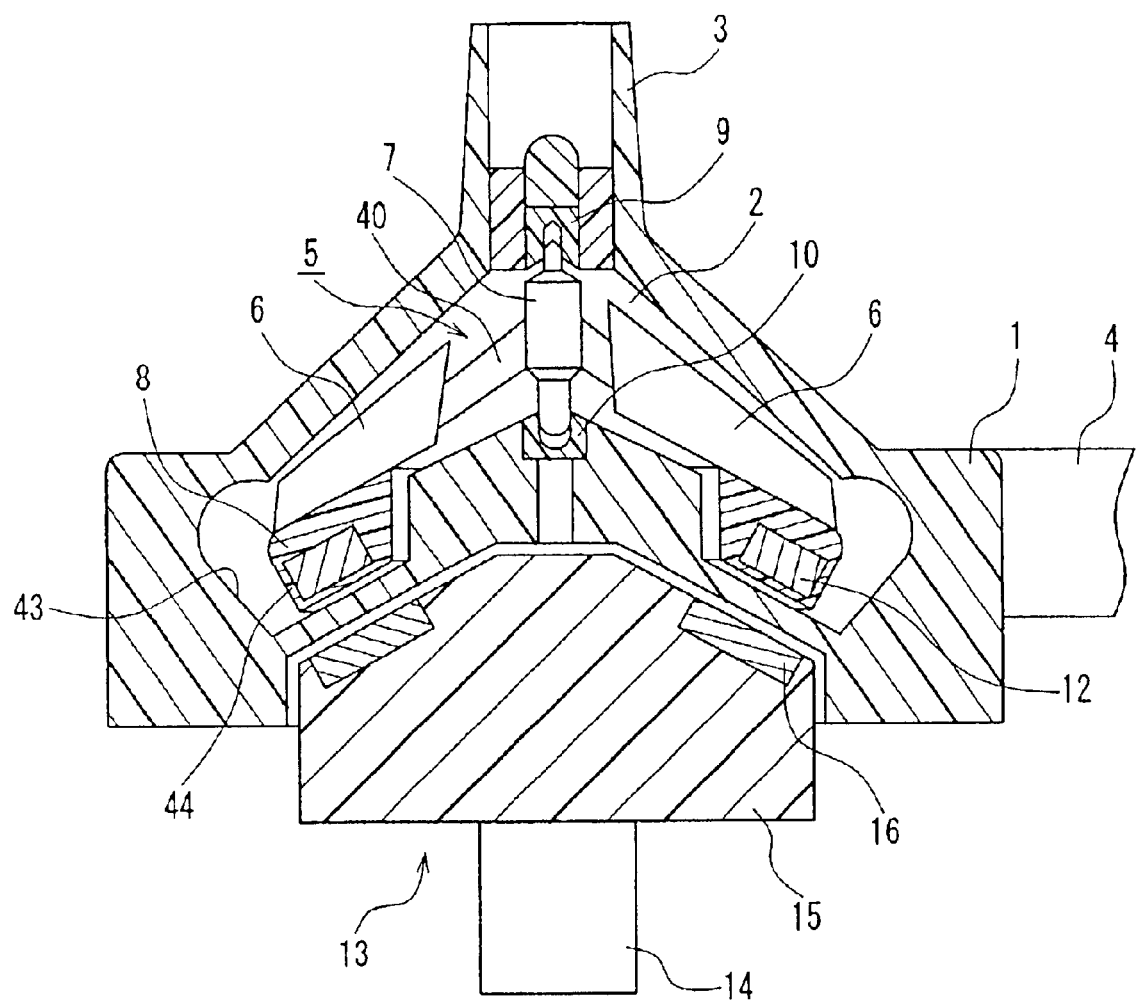
FIG. 1 is a cross-sectional view showing an example of a turbo blood pump according to the present invention.
Figure 2:
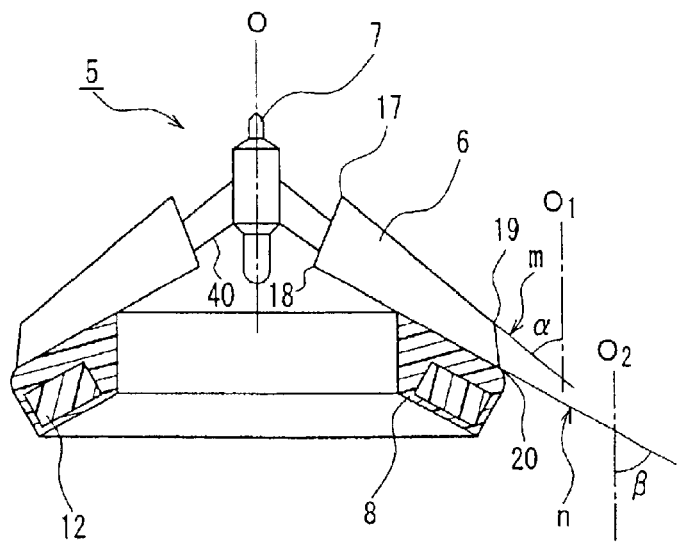
FIG. 2 is a side view showing an impeller that constitutes the turbo blood pump shown in FIG. 1.

Hereinafter, an example of the turbo blood pump of the present invention will be explained with reference to FIGS. 1 to 5. The turbo blood pump of the present invention is used mainly for medical use. FIG. 1 is a cross-sectional view showing an example of the turbo blood pump of the present invention. FIG. 2 is a side view showing an impeller that constitutes the turbo blood pump shown in FIG. 1.

Firstly, the turbo blood pump of the present invention as a whole will be explained. As shown in FIG. 1, the turbo blood pump of the present invention has a housing 1. In the housing 1, a pump chamber 2 for sucking and discharging blood is provided. The housing 1 is provided with an inlet port 3 that communicates with an upper portion of the pump chamber 2 and an outlet port 4 that communicates with a side portion of the pump chamber 2. An impeller 5 is disposed in the pump chamber 2.

As shown in FIGS. 1 and 2, the impeller 5 includes plural vanes 6, a rotation shaft 7 and an annular connection member 8. Each vane 6 is connected to the annular connection member 8 in a part at the side of the outlet port 4. Although only two vanes 6 are shown in FIGS. 1 and 2, six vanes 6 are used in this example. In the present invention, the number of the vanes is not particularly limited. As the number of the vanes 6 is increased, the discharging ability is improved accordingly. However, it becomes difficult to secure a flow path, which may cause hemolysis. Furthermore, if the number of the vanes 6 is increased, the manufacture becomes difficult. Therefore, in the present invention, it is preferable that the number of the vanes is about 4 to 8.

As shown in FIG. 1, the rotation shaft 7 is supported rotatably by an upper bearing 9 and a lower bearing 10 that are provided in the housing 1. Materials forming the rotation shaft 7, the upper bearing 9 and the lower bearing 10 are not particularly limited insofar as the material has a high abrasion resistance.

However, from the viewpoint of a high sliding property and dimensional stability, highly durable plastic such as ultra high molecular weight polyethylene, polyether ether ketone (also referred to as PEEK), etc. can be used suitably for the rotation shaft 7, the upper bearing 9 and the lower bearing 10.

If the rotation shaft 7, the upper bearing 9 and the lower bearing 10 are formed of such materials having the high sliding property and dimensional stability, the rotation shaft 7, the upper bearing 9 and the lower bearing 10 become less fatigued even after a long-time driving and exhibit excellent durability. Consequently, the turbo blood pump of the present invention can have a stable ability to transfer liquid.

Furthermore, on the lower portion of the housing 1, a rotor 13 is disposed. The rotor 13 includes a driving shaft 14 and a shaft connecting portion 15 having a substantially cylindrical shape, which are connected to each other. In an upper portion of the connecting part 15, driving magnets 16 are embedded. Although not shown in FIG. 1, a motor is connected to the driving shaft 14.

On the other hand, plural driven magnets 12 are embedded in the annular connection member 8 at constant intervals. The driven magnets 12 are attracted by the driving magnets 16 via the inner wall of the housing 1. Therefore, by the driving magnets 16 and the driven magnets 12, the impeller 5 and the rotor 13 are connected magnetically via the inner wall of the housing 1 in a state in which they are not in directly contact with each other.

Thus, when the rotor 13 is rotated by the motor, the driven magnets 12 are attracted by the driving magnets 16 and the impeller 5 is rotated together with the rotor 13. As a result, each vane 6 starts a circular motion around the rotation shaft 7 as a center, and thus the blood is transferred.

Note here that the lower surface of the annular connection member 8 in which the driven magnets 12 are embedded and the upper surface of the shaft connecting part 15 in which the driving magnets 16 are embedded are magnetically connected strongly and at the same time, are formed facing in a slanting position with respect to the rotation shaft in order to reduce hemolysis or blood stagnation sites.

Furthermore, as shown in FIG. 1, a predetermined distance is secured between the inner periphery 43 of the lower portion in the housing 1 and the outer periphery 44 of the annular connection member 8. The distance between the inner periphery 43 and the outer periphery 44 is required to be set in accordance with the rotational speed when the motor for rotating the rotor 13 is operated. If the distance between the inner periphery 43 and the outer periphery 44 is too small, hemolysis is likely to occur. On the contrary, the distance is too large, there arises a problem, for example, the amount of blood to be filled is increased.

Figure 3:
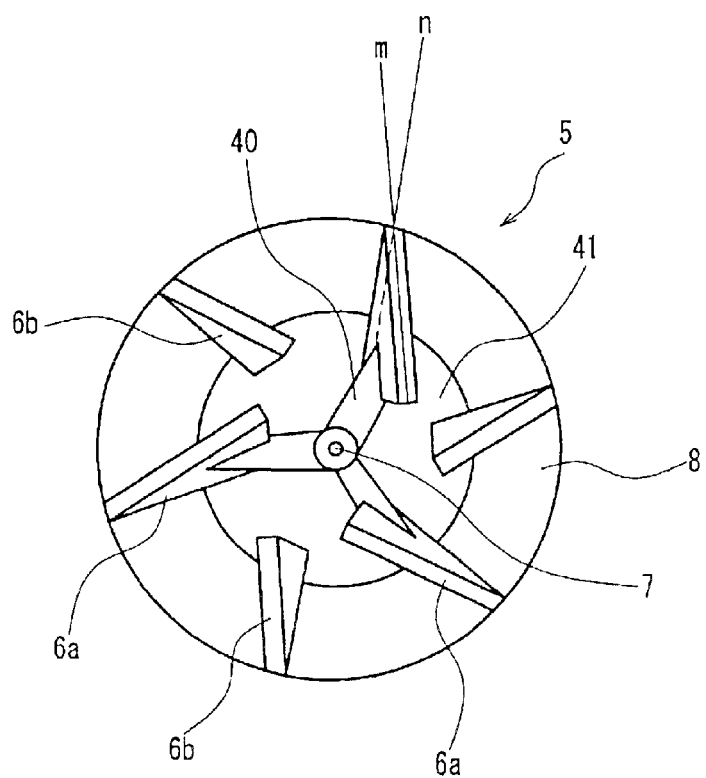
FIG. 3 is a plan view showing an impeller that constitutes the turbo blood pump shown in FIG. 1.

Next, the impeller that constitutes the turbo blood pump of the present invention will be explained in detail. FIG. 3 is a plan view showing an impeller that constitutes the turbo blood pump shown in FIG. 1. As shown in FIG. 3, both vanes 6a and vanes 6b are attached to the annular connection portion 8. In this example, three vanes 6a are formed larger than the rest of three vanes 6b and are connected to the rotation shaft 7 by supporting members 40 and on the other hand, the vanes 6b are formed smaller than the vanes 6a and are not connected to the rotation shaft 7.

The reason why only the vanes 6a are connected to the rotation shaft 7 as in this example is because if all the vanes are connected to the rotation shaft, the number of the supporting members 40 is increased, thus making it difficult to manufacture the impeller 5. Also, because the supporting member 40 hinders the flow path, if the number of the supporting members 40 is increased, the resistance becomes larger accordingly. The number of the supporting members 40 may be the minimum number capable of transmitting the rotation of the annular connection portion 8 to the rotation shaft 7. Furthermore, in this example, the reason why the sizes of the vanes are varied is to secure the flow path and to reduce the turbulence of liquid, etc.

In the example, the vanes 6a are connected to the rotation shaft 7 by means of the supporting members 40. However, the present invention is not particularly limited to this structure.

Figure 4:
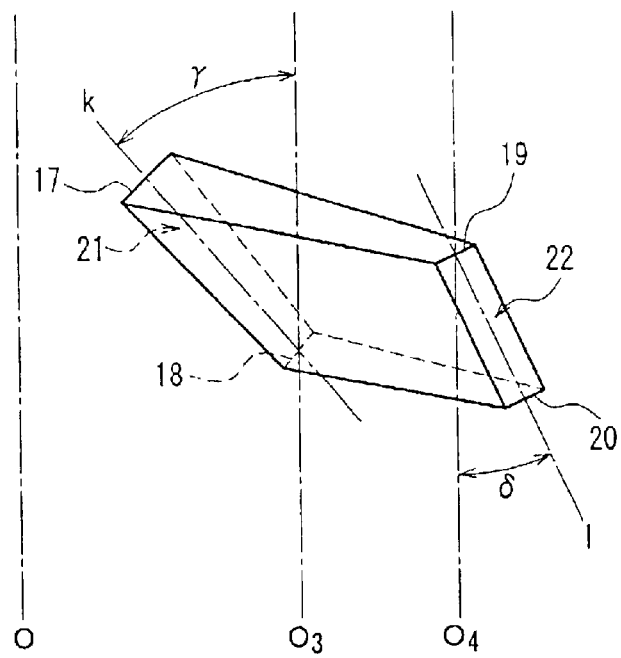
FIG. 4 is a perspective view showing a vane that constitutes the turbo blood pump shown in FIG. 1.

FIG. 4 is a perspective view showing an example of a vane that constitutes the turbo blood pump shown in FIG. 1. In FIG. 4, reference numeral 21 denotes an inlet side part of the vane 6. The inlet side part 21 is a part at the side of the inlet port 3 of the vane 6 (see FIG. 1) and is brought into contact with or collides with liquid flowing from the inlet port 3 first. Reference numeral 17 denotes an end at the upper side of the inlet side part 21 (hereinafter, referred to as "inlet side upper end") and 18 denotes an end at the lower side of the inlet side part 21 (hereinafter, referred to as "inlet side lower end"). A line k connects the inlet side upper end 17 and the inlet side lower end 18 (hereinafter, the line k will be referred to as "vane inlet side line"). Note here that the vane inlet side line k is in parallel with the longitudinal direction of the inlet side part 21 and is a center line of the inlet side part 21. Furthermore, the shape of the inlet side part 21 is a shape linear symmetric with respect to the line k.

Furthermore, reference numeral 22 denotes an outlet side part of the vane 6. The outlet side part 22 is a part of the vane 6 at the side of the outlet side part 4, and is brought into contact with or collides with liquid last. Reference numeral 19 denotes an end at the upper side of the outlet side part 22 (hereinafter, referred to as "outlet side upper end") and 20 denotes an end at the lower side of the outlet side part 22 (hereinafter, referred to as "outlet side lower end"). A line l connects the outlet side upper end 19 and the outlet side lower end 20 (hereinafter, the line l is referred to as "vane outlet side line"). Note here that the vane outlet side line 1 is in parallel with the longitudinal direction of the outlet side part 22 and is a center line of the outlet side part 22. Furthermore, the shape of the outlet side part 22 is a shape linear symmetric with respect to the line 1.

Herein, a line intersecting the vane inlet side line k and parallel to the rotation shaft is assumed to be a virtual axis o3 and a line intersecting the vane outlet side line l and parallel to the rotation shaft is assumed to be a virtual axis o4. An angle made by the vane inlet side line k and the virtual axis o3 is assumed to be $\gamma$ and an angle made by the vane outlet side line l and the virtual axis o4 is assumed to be $\delta$.

As shown in FIG. 4, in the turbo blood pump of the present invention, the vane inlet side line k and the vane outlet side line l are in the skew position with respect to each other. Furthermore, the vane inlet side line k also is in the skew position with respect to the rotation shaft (in FIG. 4, the central axis of the rotation shaft is shown by an axis o).

Therefore, in the turbo blood pump of the present invention, it is possible to set the angle $\gamma$ made by the vane inlet side line k and the virtual axis o3 to be a value that is equal or approximate to the value of the flowing angle of the blood that flows into the pump chamber 2 (see FIG. 1) through the inlet port 3 (see FIG. 1). As a result, it is possible to reduce the damage and loss of blood in the inlet part side 21, and to reduce the damage to blood cells due to the direct collision with the vane.

Furthermore, by appropriately setting the angle $\delta$ made by the vane outlet side line l and the virtual axis o4, it is possible to provide the blood discharged from the pump chamber 2 to the outlet side part 4 (see FIG. 1) with the thrust generated by rotation of the impeller efficiently, thus further improving the discharging ability.

Thus, when the turbo blood pump of the present invention is used, since it is possible to reduce hemolysis as compared with the case where a conventional blood pump is used, it is possible to rotate the impeller at a higher speed as compared with the case where the conventional blood pump is used. Therefore, it is possible to miniaturize a pump and at the same time to secure the predetermined discharging ability and the sufficient amount of blood flow. Furthermore, since the pump can be miniaturized, it is possible to reduce the amount of the blood to be filled.

In the present invention, from the viewpoint of the discharging ability, it is preferable that the angle $\delta$ is made to be smaller than the angle $\gamma$. Specifically, it is preferable that the angle $\gamma$ is set to be in the range from 20° to 40° and particularly 30°. This is because it is possible to suppress the cavitation occurring in the rear surface of the vane (a surface in the opposite side relative to the rotation direction of the rotation shaft) and to improve the reduction of hemolysis. On the other hand, it is preferable that the angle $\delta$ is approximately 0° or 0°. In other words, it is preferable that the vane outlet side line l is parallel to the rotation shaft.

Furthermore, in this example, the profile of the vane 6 presents a shape of a curved surface that smoothly connects the vane inlet side line k and the vane outlet side line 1. This shape of the curved surface is a shape obtained by shifting the vane inlet side line k, which is in the skew position with respect to the rotation shaft, toward the outer periphery of the impeller along the radius direction while allowing it to convolute until it becomes parallel to the rotation shaft. As the vane 6 has such a shape, it is possible to achieve the necessary discharging ability and at the same time to suppress the cavitation.

Furthermore, in this example, as shown in FIG. 2, the vane 6 is formed so that an angle $\alpha$ made by a line (hereinafter, referred to as "vane upper surface line") m that connects the inlet side upper end 17 and the outlet side upper end 19 of the vane 6, and a virtual axis o1 is smaller than an angle $\beta$ made by a line (hereinafter, referred to as "vane lower surface line") n that connects the inlet side lower end 18 and the outlet side lower end 20 of the vane 6 and a virtual axis o2. Note here that the virtual axis o1 in FIG. 2 intersects the vane upper surface line m and is parallel to the rotation shaft. The virtual axis o2 intersects the vane lower surface line n and is parallel to the rotation shaft.

Thus, by setting the angle $\alpha$ to be smaller than the angle $\beta$, the flow of blood in the impeller becomes a flow that is not perpendicular to the rotation shaft and not in parallel with the rotation shaft, that is, a flow that slants relative to the rotation shaft. Furthermore, since the height of the inlet side part 21 becomes larger than the height of the outlet side part 22, the cross section of the flow path at the side of the inlet port 3 having much influence on the flow amount of the pump becomes larger than the cross section of the flow path at the side of the outlet port 4.

As a result, it is possible to increase the flow amount of blood that can be processed per unit time while reducing the amount of blood to be filled in the pump. Therefore, it is possible to further improve the reduction of hemolysis mentioned above. Note here that from the viewpoint of the improvement in the reduction of hemolysis, the angle $\alpha$ is preferably in the range from 45° to 60°. The angle $\beta$ is preferably in the range from 60° to 80°.

Figure 5:
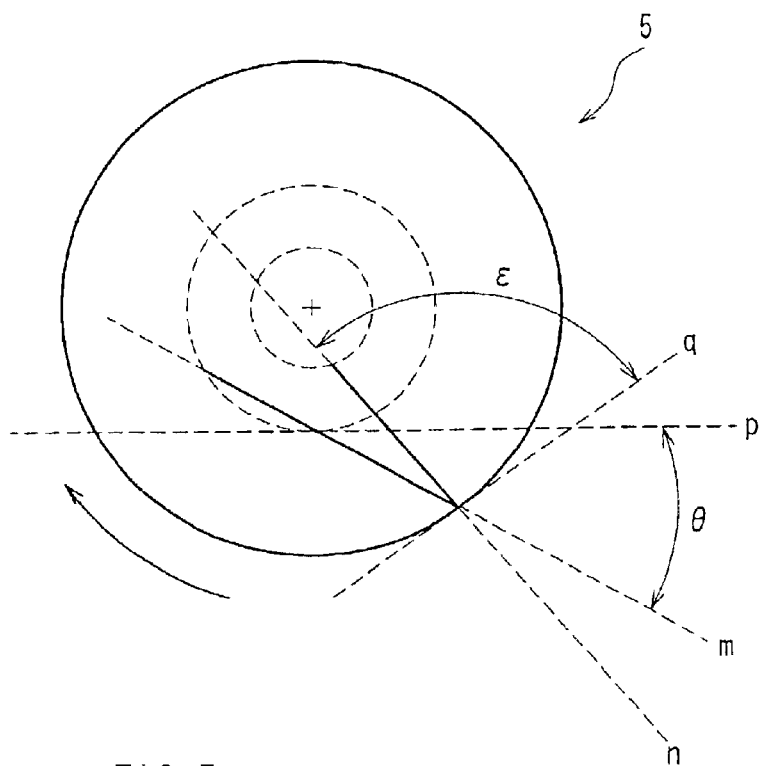
FIG. 5 is a view schematically showing the position where the vanes are attached, seen from the upper portion of the impeller.

FIG. 5 is a schematic view showing a position where an impeller is attached to the vane shown in FIG. 4 seen from the upper part of the impeller. In FIG. 5, p denotes a tangent line passing an intersection point between the circle passing the inlet side upper end 17 of each vane (see FIG. 4) and the vane upper surface line m of the arbitrary vane in this circle; and q denotes a tangent line passing an intersection point between the circle passing the outlet side lower end 20 of each vane (see FIG. 4) and the vane lower surface line n of the arbitrary vane in this circle. Note here that the above-mentioned two circles are concentric with the outer periphery of the impeller.

Herein, when an angle made by the vane upper surface line m and the tangent line p is assumed to be θ and an angle made by the vane lower surface line n and the tangent line q is assumed to be ε, since the vane is formed so that the angle θ is smaller than the angle ε in this example as shown in FIG. 5, the vane upper surface is positioned at the side in the direction in which the impeller is rotated with respect to the vane lower surface.

Therefore, it is possible to further reduce the loss of blood due to collision with the inlet side part 21. In addition, it is possible to reduce the separation of blood and the generation of eddy (generation of cavitation) at the rear surface of the vane. Therefore, it is possible to further improve the reduction of the hemolysis as mentioned above.

In the present invention, materials for the impeller and the housing, that is, the components of the turbo blood pump are not particularly limited. However, from the viewpoint of lightening, easy moldability, strength, stability in dimension, etc., it is preferable that a synthetic resin such as polycarbonate, polyethylene terephthalate, polysulfone, etc. is used.

In the turbo blood pump of the present invention, as shown in FIGS. 1 to 5, a hole is provided in the central portion of the annular connection portion 8 that constitutes the impeller 5, and the vane 6 has a shape of a curved surface. Therefore, the structure of the turbo blood pump of the present invention has a structure in which the blood is not likely to stagnate in the impeller. In other words, in the turbo blood pump of the present invention, in structure, thrombus is not likely to be formed. Therefore, the turbo blood pump of the present invention is effective in a long-time extracorporeal circulation.

Furthermore, in the present invention, in order to further prevent the formation of thrombus inside the pump chamber, it is preferable that all of the constituent components such as an inner surface of the housing or an outer surface of the impeller, etc., brought into contact with blood in the pump chamber are subjected to anticoagulation treatment.

The method for anticoagulation is not particularly limited. However, there is, for example, a method for allowing antithrombotic mucopolysaccharide to be ionically bonded the surface that is in contact with blood. This method is widely applied and effective. Specifically, as disclosed in JP 11(1999)-99485A of the present applicant, a complex of heparin and quaternary ammonium salt is coated on the surface of plastic.

In some of the conventional turbo blood pumps, driven magnets for transmitting the rotation of the driving shaft to the rotation shaft of the impeller are housed in a space other than the pump chamber. In this case, it is necessary to provide a shaft seal for shielding between the pump chamber and the space housing the driven magnets. However, in a case where such a shaft seal is provided, it is necessary to consider taking measures against blood leakage, thus causing some problems, for example, the heating of the shaft seal and the formation of thrombus.

With respect to this, in this example, as mentioned above, the driven magnets 12 are attached to the annular connection portion 8 and the annular connection portion 8 is housed in the pump chamber. Therefore, it is not necessary to provide a shaft seal as in the conventional structure, thus avoiding problems as mentioned above.

EXAMPLE

Figure 6:
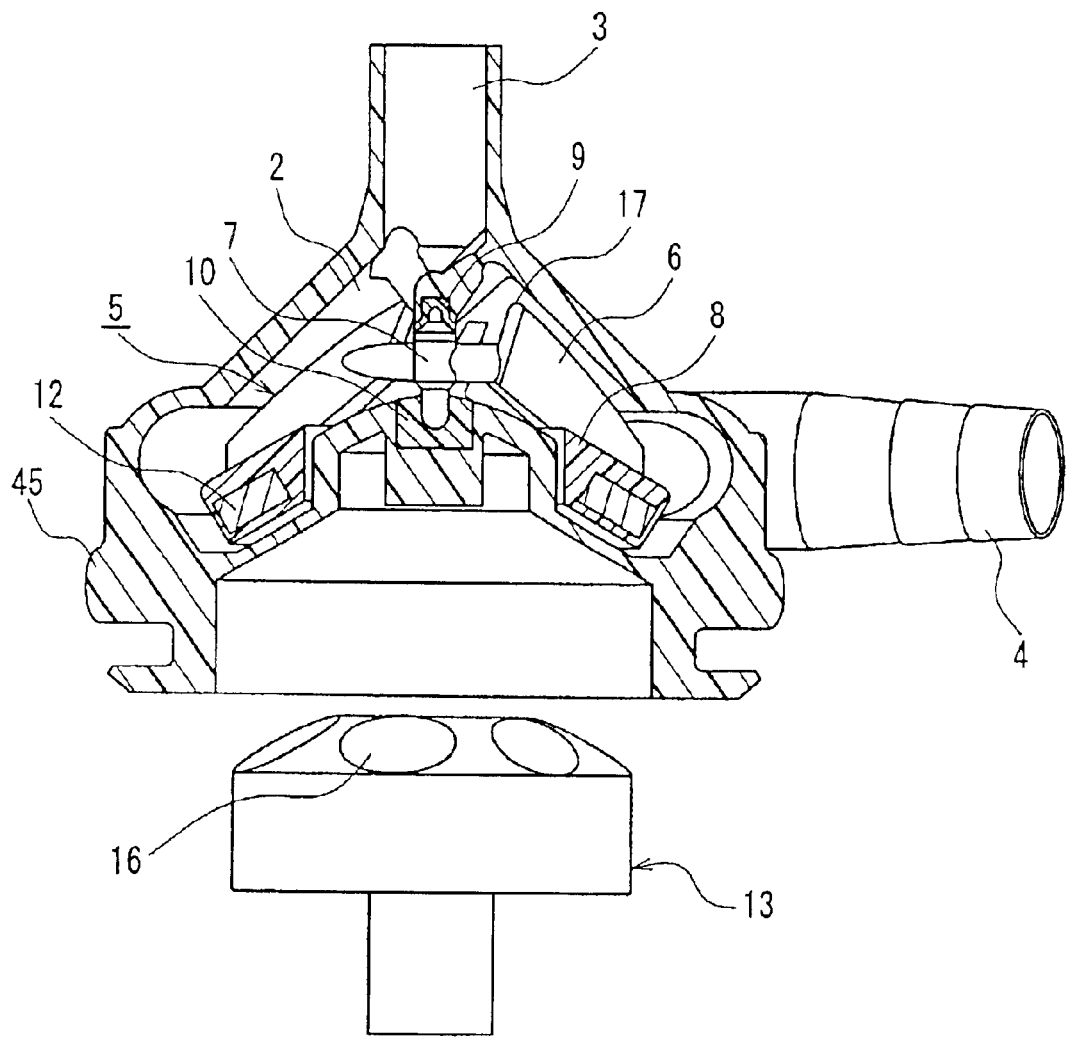
FIG. 6 is a cross-sectional view showing another example of a turbo blood pump of the present invention.

FIG. 6 is a cross-sectional view showing another example of the turbo blood pump of the present invention. In FIG. 6, components to which the same reference numbers are given as in FIG. 1 are configured similar to the components shown in FIG. 1. The turbo blood pump shown in FIG. 6 is configured in the same manner as the turbo blood pump shown in FIG. 1 except that the shape of the inside the housing 45 is different from the shape of the inside the housing 1.

In the turbo blood pump shown in FIG. 6, the outer diameter and the height of the housing 45 are set to be 58 mm and 56 mm, respectively. The weight of the housing 45 is set to be 43 grams. Furthermore, the amount of blood to be filled in the pump chamber 2 is 20 mL. The housing 45 and the impeller 5 are formed of resin materials such as polycarbonate. Furthermore, the rotation shaft 7 is formed of stainless steel, and the upper bearing 9 and the lower bearing 10 of the rotation shaft 7 are formed of PEEK mentioned above.

Furthermore, in the turbo blood pump shown in FIG. 6, the angle α made by the vane upper surface line m and the virtual axis o1 is set to be 45°, and the angle α made by the vane lower surface line n and the virtual axis o2 is set to be 60° (see FIG. 2). Furthermore, the angle γ made by the vane inlet side line k and the virtual axis o3 is set to be 30° and the angle δ made by the vane outlet side line l and the virtual axis o4 is set to be 0° (see FIG. 4). Furthermore, the angle θ made by the vane upper surface line m and the tangent line p is set to be 26° and the angle ε made by the vane lower surface line n and the tangent line q is set to be 950 (see FIG. 5).

Furthermore, in the turbo blood pump shown in FIG. 6, the diameter of the outer periphery of the annular connection portion 8 is set to be 40 mm and the diameter of the inner periphery of the annular connection portion 8 is set to be 22 mm. Furthermore, the height from the upper end of the surface of the inner periphery of the annular connection portion 8 to the inlet side upper end 17 (height of the vane inlet port) is set to be 11 mm and a full length of the rotation shaft is set to be 10 mm.

By using the turbo blood pump shown in FIG. 6, discharging of blood was carried out. When the flow amount of blood was 5 L/min, the hemolytic index at the lift of 100 mmHg was about 0.0009 g/100 L. This value is sufficiently lower as compared with the hemolytic index 0.0045 g/100 L when using a "Bio-pump" (product of Bio Medicus) or the hemolytic index 0.0103 g/100 L when using "Delphin Pump" (product of TERUMO CORPORATION) under the same conditions.

Similarly, when the flow amount of blood was 5 L/min, the hemolytic index at the lift of 200 mmHg was about 0.0041 g/100 L. This value is sufficiently lower as compared with the hemolytic index 0.0078 g/100 L when using the Bio Pump or the hemolytic index 0.0145 g/100 L when using the Delphin Pump under the same conditions.

The invention may be embodied in other forms without departing from the spirit or essential characteristics thereof.

The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. A turbo blood pump, comprising
a housing having an inlet port and an outlet port; and
an impeller disposed rotatably in the housing;
wherein the impeller comprises at least a rotation shaft, plural vanes and an annular connection portion, the plural vanes are connected to the annular connection portion in a part at the side of the outlet port, and at least some of the plural vanes are connected to the rotation shaft by a supporting member in a part at the side of the inlet port;
a vane inlet side line of the plural vanes, which connects an inlet side upper end and an inlet side lower end of the plural vanes, is in a skew position with respect to the rotation shaft and a vane outlet side line of the plural vanes, which connects an outlet side upper end and an outlet side lower end of the plural vanes; and
an angle made by the vane inlet side line and an axis intersecting the vane inlet side line and parallel to the rotation shaft is set to be larger than an angle made by the vane outlet side line and an axis intersecting the vane outlet side line and parallel to the rotation shaft.

2. The turbo blood pump according to claim 1, wherein the vane outlet side line is parallel to the rotation shaft.

3. The turbo blood pump according to claim 1, wherein an angle made by a vane upper surface line that connects the inlet side upper end and the outlet side upper end, and an axis intersecting the vane upper surface line and parallel to the rotation shaft is set to be smaller than an angle made by a vane lower surface line that connects the inlet side lower end, and the outlet side lower end and an axis intersecting the vane lower surface line and parallel to the rotation shaft.

4. The turbo blood pump according to claim 1, wherein assuming a first circle passing the inlet side upper end, which is concentric with the outer periphery of the impeller, a tangent line of the first circle, which passes an intersection point of a vane upper surface line of one vane and the first circle, a second circle passing the outlet side lower end, which is concentric with the outer periphery of the impeller, and a tangent line of the second circle, which passes an intersection point of a vane lower surface line of the one vane and the second circle,
an angle made by the tangent line and the vane upper surface line of the one vane is smaller than an angle made by the tangent line and the vane lower surface line of the one vane.

5. The turbo blood pump according to claim 1, wherein the profile of the vane presents a shape of a curved surface that smoothly connects the vane inlet side line and the vane outlet side line,
the shape of the curved surface is a shape obtained by shifting the vane inlet side line that is in the skew position with respect to the rotation shaft along the radius direction toward the outer periphery of the impeller while allowing it to convolute until it becomes parallel to the rotation shaft.

6. The turbo blood pump according to claim 1, wherein the plural vanes include a first vane and a second vane, which have different areas.

7. The turbo blood pump according to claim 6, wherein the first vane and the second vane are disposed so that they are in position of rotational symmetry with respect to the rotation shaft and the total number of the plural vanes is in the range from 4 to 8.

8. The turbo blood pump according to claim 1, comprising a driving shaft having driving magnets at the side of the housing outside the housing,
wherein the annular connection portion is housed in a pump chamber in the housing and has driven magnets to be attracted by the driving magnets via the inner wall of the housing.

9. A turbo blood pump, comprising
a housing having an inlet port and an outlet port; and
an impeller disposed rotably in the housing,
wherein the impeller comprises at least a rotation shaft, plural vanes and annular connection portion, the plural vanes are connected to the annular connection portion in a part at the side of the outlet port, and at least some of the plural vanes are connected to the rotation shaft by a supporting member in part at the side of the inlet port; and
a vane inlet side line of the plural vanes, which connects an inlet side upper end and an inlet side lower end of the plural vanes, is in a skew position with respect to the rotation shaft and a vane outlet side line of the plural vanes, which connects an outlet side upper end and an outlet side lower end of the plural vanes.

* * * * *